US006486354B1

(12) United States Patent
Gani et al.

(10) Patent No.: US 6,486,354 B1
(45) Date of Patent: Nov. 26, 2002

(54) SOLID PHASE SUPPORTS

(75) Inventors: David Gani, Birmingham (GB); Friedrich Erich Karl Kroll, Hagersten (SE); Michael John Plater, Aberdeen (GB); John Richard Morphy, Dune Pershire (GB); David Rees, Glasgow (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/485,613

(22) PCT Filed: Aug. 13, 1998

(86) PCT No.: PCT/EP98/05283

§ 371 (c)(1),
(2), (4) Date: Apr. 17, 2000

(87) PCT Pub. No.: WO99/09073

PCT Pub. Date: Feb. 25, 1999

(30) Foreign Application Priority Data

Aug. 13, 1997 (GB) ............................................. 9717173

(51) Int. Cl.[7] .................... C07C 315/00; C07C 317/00; C07C 43/11; G01N 33/53; G01N 33/543

(52) U.S. Cl. ........................... 568/33; 435/7.1; 435/7.2; 435/DIG. 40; 435/DIG. 42; 436/501; 436/518; 530/333; 530/334; 530/335; 540/139; 568/28; 568/32; 568/621; 568/622; 568/623

(58) Field of Search ...................... 435/717.2, DIG. 40, 435/DIG. 42; 436/501, 518; 530/333–335; 540/139; 568/32, 621–623, 28, 33

(56) References Cited

U.S. PATENT DOCUMENTS

| 4,575,541 A | 3/1986 | Carpino |
| 4,659,774 A | 4/1987 | Webb |
| 5,616,687 A | 4/1997 | Desai |
| 5,912,342 A | * 6/1999 | Heinonen et al. ........... 540/139 |

FOREIGN PATENT DOCUMENTS

| EP | 0 008 100 A | 2/1980 |
| EP | 0 273 895 A | 7/1988 |
| EP | 0 285 562 A | 10/1988 |
| EP | 0 591 807 A | 4/1994 |
| EP | 0 687 691 A | 12/1995 |
| WO | WO 95 34813 A | 12/1995 |

OTHER PUBLICATIONS

Tesser et al. Synthesis of 2–Hydroxyethylsulfonyl–methyl–Substituted Polystyrenes and their Application in Solid Phase Peptide Synthesis. Tetrehedron, May 1976, vol. 32, No. 9, pp. 1069–1072.*

F.E.K. Kroll: "Resin–Immobilised Benzyl and Aryl Vinyl Sulfones: New Versatile Traceless Linkers for Solid–Phase Organic Synthesis." vol. 38, No. 49 Oct. 2, 1997.

* cited by examiner

Primary Examiner—Jyothsna Venkat
Assistant Examiner—Maurie Garcia Baker
(74) Attorney, Agent, or Firm—William P. Ramey, III

(57) ABSTRACT

Embodiments of the present invention generally relate to carrying out organic chemistry on solid supports comprising derivatised functionalities, methods for synthesizing said supports, methods for synthesizing compounds comprising amine groups or N-containing heterocycles using said solid supports, intermediate compounds linked to said supports and uses thereof.

1 Claim, No Drawings

SOLID PHASE SUPPORTS

Related Application

This application is a continuing application of application Ser. No. 09/485,195, filed on May 4, 2000, which is a national stage filing of an international application, application number PCT/GB98/02264, filed on Aug. 5, 1998.

FIELD OF THE INVENTION

The present invention relates to carrying out organic chemistry on solid supports comprising derivatised functionalities, methods for synthesising said supports, methods for synthesising compounds comprising amine groups or N-containing heterocycles using said solid supports, intermediate compounds linked to said supports and uses therefor. In particular, the invention relates to solid supports comprising derivatised amide or sulphone groups, methods for synthesising said supports, methods for synthesising compounds comprising tertiary amine groups or N-containing heterocyclic compounds using said supports and intermediate compounds comprising quaternary ammonium groups linked to said supports and uses therefor.

BACKGROUND OF THE INVENTION

Solid phase chemistry is well known in the art, particularly in the fields of peptide and oligonucleotide synthesis. Advantages associated with solid phase synthesis include the ability to drive reactions to completion by use of excess reagents, ease of work up and potential automation of synthetic procedures. Organic compounds have traditionally been attached to the solid support by certain cleavable linker groups which yield, on cleavage, compounds in which polar functionality remains at the point of attachment, for example a $CO_2H$, $OH$, $NH_2$, $CONH_2$ or a $CONHR$ group. The synthesis of non-oligomeric organic compounds using resin-bound synthetic routes is a key component of the emerging technology of combinatorial chemistry (Gordon, E. M.; Barrett, R. W.; Dower, W. J.; Fodor, S. P. A.; Gallop, M. A. *J. Med. Chem.* 1994, 37, 1385–1401; Lowe, G. *Acc. Chem. Res.* 1995, 24, 309–317; Fruchtel, J. S.; Jung, G. *Angew. Chem. Int. Ed. Engl.* 1996, 35, 17–42).

One of the current limitations of this approach is the requirement for a "handle" to link small organic molecules onto a polymeric resin. In Merrifield peptide synthesis, for example, a carboxylic acid is linked via an ester group. Recently the range of linkers has increased (Fruchtel, J. S., and Jung G. supra).

Morphy J. R. et al. *Tetrahedron Letters*, 1996, 37, 3209–3212 report a novel linker strategy and describe a new type of linker and release system for resin-bound synthesis which is based upon Michael addition and Hofmann elimination (β-elimination) reactions. The synthetic route is outlined in the following Scheme below:

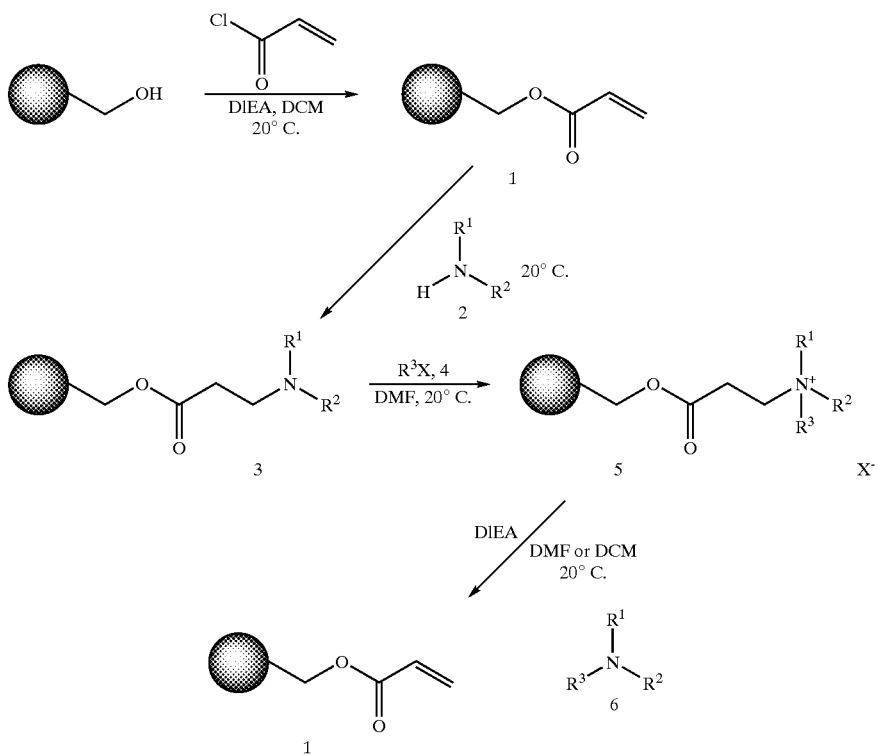

where $R^1$, $R^2$ $R^3$ each represent an alkyl group and X is Br or I. Where $3^a$ is a secondary amine ($R^2$=H), conversion to a tertiary amine is achieved by reductive alkylation on the resin using a suitable aldehyde and $NaBH(OAc)_3$ in 1% acetic acid/dimethylformamide for 18 hours at 20° C.

The outlined synthetic route above utilises hydroxymethyl polystyrene resin derivatised with acryloylchloride to the acrylate ester 1. Michael addition of a secondary amine 2 gives the resin-bound tertiary amine 3. Alternatively, a primary amine 2 ($R^2$=H) gives a resin-bound secondary amine which is converted into the tertiary amine 3 ($R^2$=alkyl) by reductive alkylation. Quaternisation of the tertiary amine 3 with an alkyl halide 4 to give 5 introduces another site of diversity and activates the linker for cleavage by a facile Hofmann elimination reaction. Thus $iPr_2NEt$ (diisopropylethylamine; DIEA) at room temperature liberates the tertiary amine 6 into solution and regenerates the resin 1.

Since the resin linker 1 is regenerated after cleavage of the product and is functionalised via a Michael reaction, the resin is referred to as a REM resin (Morphy, supra).

A disadvantage of the above outlined reaction is that the ester derivatised resin, in this case originating from an acrylate ester, can be unstable under certain reaction conditions such as strong acid, strong base, or others reaction conditions including reagents such as Grignard reagents, and reducing agents such as $LiAlH_4$ and the like. In such reaction conditions, cleavage at the ester bond may occur. Thus, the general applicability of the ester derivatised resin can be limited. and as a consequence, the solid phase synthesis of desired amine-containing compounds or N-containing heterocyclic compounds may not be realised.

SUMMARY OF THE INVENTION

The present invention seeks to mitigate against the disadvantages associated with the prior art and to provide derivatised solid supports which are stable to a wide range of chemistries and whereon a broad scope of amines or N-heterocyclic containing compounds can be prepared utilising the Hoffmann elimination reaction, as described above, to release the amines from the solid supports.

DETAILED DESCRIPTION OF THE INVENTION

According to a first variant of the invention there is provided a solid support comprising a functionalised amide according to Formula (I).

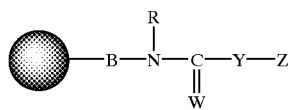

(I)

wherein

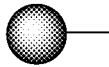

represents the solid support;

B is a conventional spacer arm or a bond;

R is selected from H, $(C_1-C_6)$alkyl, optionally substituted with halogen. aryl$(C_1-C_6)$alkyl and aryl, optionally substituted with $(C_1-C_6)$alkoxy, OH or halogen;

W is selected from O and S;

Y is $CHR^4$ where $R^4$ is selected from H, $(C_1-C_4)$alkyl, optionally substituted with halogen, and phenyl, optionally substituted with $CF_3$, $(C_1-C_6)$alkoxy;

Z is $CR^5R^6$—L where $R^5$ and $R^6$ are independently selected from H, $(C_1-C_4)$-alkyl, and phenyl; L is a leaving group; or Y and Z together form $CR^4=CR^5R^6$ wherein $R^4$ and $R^5$ are as defined above, or wherein $R^4$ and $R^5$ together with the carbon atoms to which they are bonded form a $(C_4-C_8)$cycloalkene ring.

The term $(C_1-C_6)$-alkyl as used in the definition of formula I means a straight or branched-chain alkyl group having from 1 to 6 carbon atoms, such as methyl, ethyl, propyl, isopropyl, butyl, pentyl and hexyl.

The term $(C_1-C_4)$alkyl means, likewise, a straight or branched-chain alkyl group having 1–4 carbon atoms.

The term $(C_1-C6)$alkoxy means a $(C_1-C_6)$alkyloxy group, wherein $(C_1-C_6)$alkyl has the previously given meaning. A preferred $(C_1-C_6)$alkoxy group is methoxy. Preferred $(C_1-C_6)$alkoxy substituted aryl groups are 2-methoxyphenyl and 4-methoxyphenyl.

The term halogen means F, Cl, Br or I.

The term aryl means an aromatic ring system having from 6–12 carbon atoms, such as for example phenyl and naphthyl; a preferred aryl group is phenyl.

The term aryl$(C_1-C_6)$alkyl as used in the definition of formula I means an aryl group, having the meaning as previously defined, linked to a $(C_1-C_6)$alkyl group as previously defined, such as benzyl (phenylmethyl).

The term $(C_4-C_8)$cycloalkene ring, as used in the definition of formula I means a cycloalkene ring having 4–8 carbon atoms, like cyclobutene, cycloheptene, cyclohexene, cycloheptene and cyclooctene.

The term leaving group is known in the art of substitution reactions (Advanced Org. Chem (1992) (4th Ed.) March J, p 352, Wiley and Sons). Examples of well known leaving groups are Cl, Br, I, tosyloxy, mesyloxy, trifluoromethanesulphonyloxy, trifluoroethanesulphonyloxy (tresyloxy) and the like.

The conventional spacer arm B, as used in the definition of Formula I, means a chemical structure linking (or interspaced between) a functional group to the backbone structure of the solid support. B may be any conventional spacer arm commonly employed in solid phase organic chemistry. For instance, the spacer arm B of a chloromethylated or an aminomethylated polystyrene divinylbenzene (Merrifield) resin, is the methylene, —$CH_2$— group. Further examples of spacer arms B are $(CH_2)_n$, $CH_2(OCH_2CH_2)_n$ wherein n=0, 1, 2, 3 or 4, $CH_2C(CH_3)(PEG)_2$, PEG (polyethyleneglycol)-$CH_2$ and the like. Examples of these and other suitable spacer arms can be found in The Combinatorial Chemistry Catalog, February 1997 (NovaBiochem) pp1–37.

In a preferred embodiment of the first main aspect of the invention, B is selected from $(CH_2)_n$ and $CH_2(OCH_2CH_2)_n$ and n is 0, 1 or 2; R is selected from H, $(C_1-C_4)$alkyl and phenyl; W is O; and Y and Z together form $CR^4=CR^5R^6$ wherein $R^4$, $R^5$ and $R^6$ are independently selected from H, $CH_3$ and phenyl; or Y is $CHR^4$ where $R^4$ is selected from H, $CH_3$ and phenyl and Z is $CR^5R^6$—L where L is a leaving group selected from Br, Cl, I, tosyloxy, mesyloxy and trifluoromethanesulphonyloxy.

In a further preferred embodiment, B is $CH_2$; R is selected from H, $CH_3$, $C_2H_5$, $C_3H_7$ (ie straight or branched-chain), and phenyl; W is O; and Y and Z together form $CH=CH_2$ or Y is $CH_2$ and Z is $CH_2$—L where L is a leaving group selected from Br, Cl, I, tosyloxy, mesyloxy, and trifluoromethanesulphonyloxy.

In a particular preferred embodiment B is $CH_2$; R is H; W is O; Y—Z is $CH=CH_2$, and the solid support is the polystyrenedivinylbenzene support of a Merrifield resin.

The selection of a solid support may be made from conventional commercially available solid support materials such as resins, for example, aminomethyl polystyrene and the like. Other suitable solid support resins for use in the present invention can be found in, for example, The Combinatorial Chemistry Catalog, supra. Suitable solid supports include polystyrene optionally cross-linked with a cross-linking agent such as divinyl-benzene, acrylamides such as polyacrylamide, dimethylacrylamide, and polystyrene acrylamide, glass, silica gels, polyethylene glycol (PEG), polyethylene glycol-polystyrene (PEG-PS) resin, ARGO-GEL™ (Argonaut Tech. Inc.), cellulose, pore-glass, for example, is the form of pore-glass, beads, latex, and macroporous supports and the like.

The solid support as used in the invention may be in various physical forms, such as in the form of beads, the most commonly used polystyrene based resins (The Combinatorial Chemistry Catalog, vide supra), pins, such as polypropylene/polyethylene pins and the like; pellets; disks; capillaries; hollow or solid fibres. The solid support may be flat, or alternatively; or other shaped may be in the form of substantially spherical; beads, such as a polygonal shape, for example a hexagon.

The person skilled in the art will appreciate that the selection of a solid support will depend on the reaction conditions employed and/or envisaged in the synthesis of desired amines or N-heterocyclic containing compounds. Supports may be selected as appropriate with a view to such factors as the mildness or harshness of the reaction conditions employed. Macroporous solid supports can be viewed as those types wherein the structure remains substantially permanently swollen, irrespective of the choice of solvent. For example, those containing as the base material. polystyrene, styrene-divinylbenzene copolymer, glass, silica gel, polypropylene, polyvinyl alcohol, poly(2-hydroxyethyl methacrylate), oligo(ethyleneglycol) dimethacrylate polymer, polyacrylamide and Kiesel-guhr. Preferred supports include polystyrene cross-linked to varying degrees with divinylbenzene to give either a microporous or macroporous support, polyethyleneglycol (PEG) or PEG-derivatised polystyrene. Such supports may either be in the form of supports functionalised with appropriate groups such as NHR or functionalised with groups which may be converted to such NHR groups. The selection of solid support is not critical provided that it comprises appropriate NHR groups or is a solid support comprising groups capable of being functionalised to NHR groups. Such supports are known to the person skilled in the art, such as those made by converting a chloromethylated polystyrene resin to an amino functionalised resin via an appropriate alkylation reaction.

Generally, an amide-functionalised support of Formula (I) can be prepared from a suitable solid support such as a resin comprising an amine group, of Formula (II):

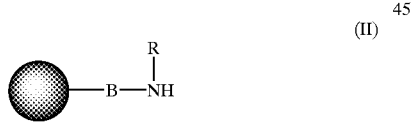

(II)

where B and R are as defined hereinabove, by acylation with a suitably activated acid derivative according to formula Y—Z—COOH, wherein Y and Z are as defined above, such as an activated ester derivative or an acid chloride derivative, after which the resulting amide may be optionally converted to a thioamide, for instance, by treatment with phosphorous pentasulfide. For instance, an amide functionalised support of Formula I can be prepared from a suitable so. support of Formula II by the addition of a suitable carbonyl chloride, such as an acid chloride, for example, acryloyl chloride or 3-bromopropionoyl chloride, under suitable reaction conditions, for example, in the presence of a tertiary amine base, such as diisopropyl ethyl amine (DIEA) in a suitable organic solvent, such as dichloromethane. Such reaction conditions are familiar to the man skilled in the art.

In a second aspect of the invention, there is provided a process for the preparation of a tertiary amine which comprises:

(i) adding a primary or secondary amine to an amide-functionalised support according to Formula (I) by way of a Michael addition to an unsaturated amide or by alkylating a propionamide having a leaving group L in the 3 position:

(ii) adding an alkylating agent to the product of step (i); and (iii) performing a Hofmann elimination on the quaternary ammonium compound generated in step (ii).

In a variant of the second aspect of the invention there is provided a process for the preparation of a tertiary amine which comprises:

(i) adding a primary amine to an amide-functionalised support according to Formula (I) by way of a Michael addition to an unsaturated amide or by alkylating a propionamide having a leaving group L in the 3 position;

(ii) performing a reductive alkylation on the secondary amine produced in step (i) giving a tertiary amine;

(iii) adding an alkylating agent to the product of step (ii); and (iv) performing a Hofmann elimination on the quaternary ammonium compound generated in step (iii).

Reference is made to the outline reaction Scheme 1, below:

SCHEME 1

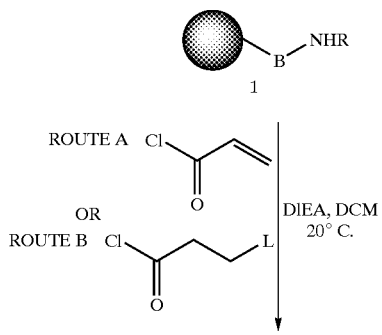

-continued

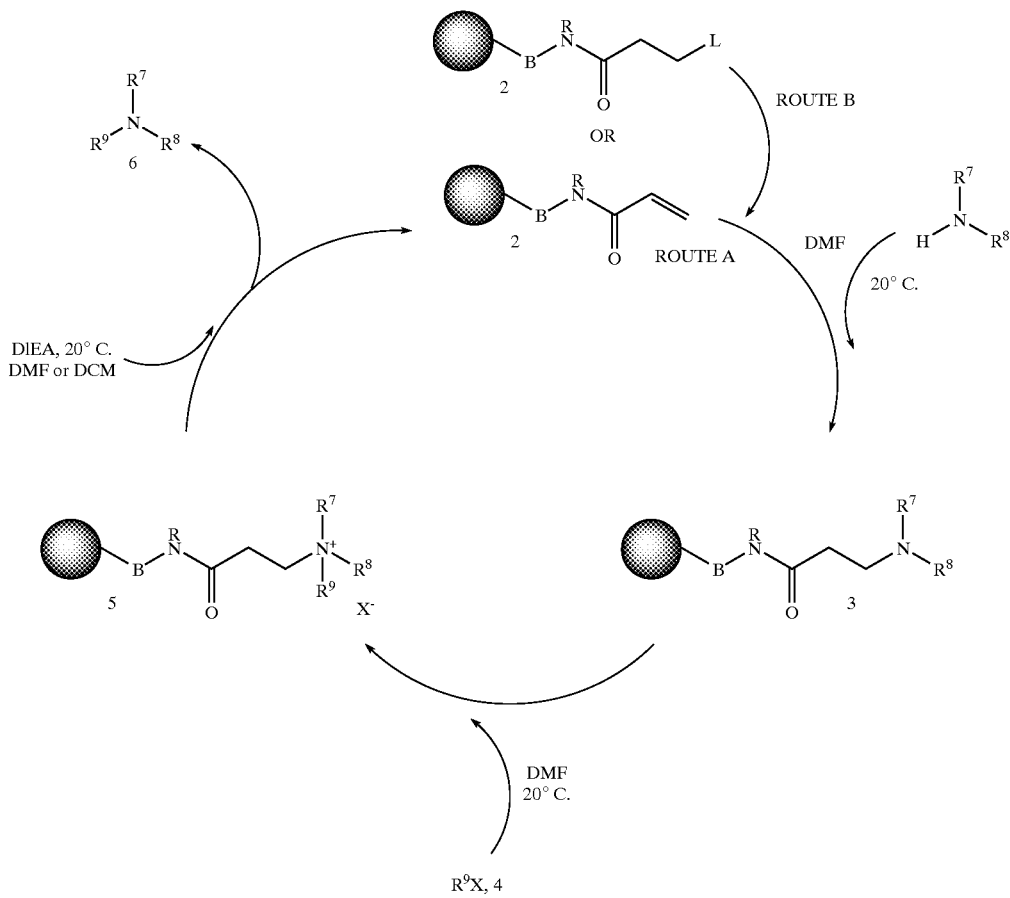

The primary or secondary amine $HNR^7R^8$ may be any primary or secondary amine capable of undergoing a Michael addition to the amide-functionalised resin giving 3 (Route A).

$R^7$ and $R^8$ may be selected from H, branched or straight chain $(C_1-C_6)$alkyl such as methyl, ethyl, propyl, isopropyl, butyl, and sec.butyl, $(C_1-C_6)$alkyl ethers such as methyloxyethyl, arylalkyl such as phenylethyl, $(C_1-C_6)$ alkyl-O—$(C_1-C_6)$alkylene, vinyl $(C_1-C_6)$ alkylene, such as allyl and the like.

Alternatively, $R^7$ and $R^8$ may form part of a ring structure, for example, in secondary amines such as ethyl isonipecotate (ethyl 4-piperidinecarboxylate), 4-benzyl piperidine, piperazine such as 1-phenyl piperazine, 1,2,3,4-tetrahydroisoquinoline, and proline. In general, the secondary amine can be any secondary amine which can be employed in a Michael addition reaction leading to compound 3.

The alkylating agent may be any alkylating agent such as an alkylating agent of the formula $R^9X$, where X is selected from I, Br, Cl, trifluoromethanesulphonyloxy, and $R^9$ is an alkyl group which can be added to compound 3 in the synthesis of the quaternary compound 5. Suitable $R^9$ alkyl groups include branched or straight chain $(C_1-C_6)$alkyl such as methyl, ethyl, propyl, n-butyl, $(C_1-C_6)$alkyl ethers such as methyloxyethyl, arylalkyl such as phenylmethyl, $(C_1-C_6)$ alkyl-O—$(C_1-C_6)$alkylene, vinyl$(C_1-C_6)$alkylene, such as allyl and the like. The person skilled in the art will appreciate that generally the selection of $R^7$, $R^8$ and $R^9$ is such that the groups are ones which are capable of being utilised in the generation of tertiary amines in the solid phase syntheses described herein. When selecting $R^7$ and $R^8$ groups when these relate to branched chain substituents, the skilled addressee will appreciate that a branch point comprising a quaternary carbon will not be located on an atom adjacent to the N.

It will be appreciated that, in addition to the three characteristic steps of the methodology (Michael addition, quaternisation, Hofmann), it is possible to add extra steps to elaborate the structure of the bound compound (for example, structure 3 of Scheme 1; structure 3 of Scheme 4) and thereby expand the diversity of a combinatorial library or array. As such, the man skilled in the art will also appreciate that the solid supports of the invention may be adapted for use in peptide synthesis, oligonucleotide synthesis and the like.

For example, an amine $R^7R^8NH$ may be added to the resin, then $R^8$ may be elaborated to $R^{10}$, for example, via an addition or displacement reaction such as described by Hermkens P. H. H. et al. Tetrahedron 53 5643–5678, 1997. Quaternisation with an $R^9X$ and base catalysed cleavage may then provide an elaborated amine $NR^7R^9R^{10}$ as outlined in scheme 2 below. A specific example would be the addition of ethyl isonipecotate to the resin, then addition of MeMgBr, quaternisation with methyl iodide, and cleavage with DIEA, giving compound (2) (see Scheme 2 below).

SCHEME 2

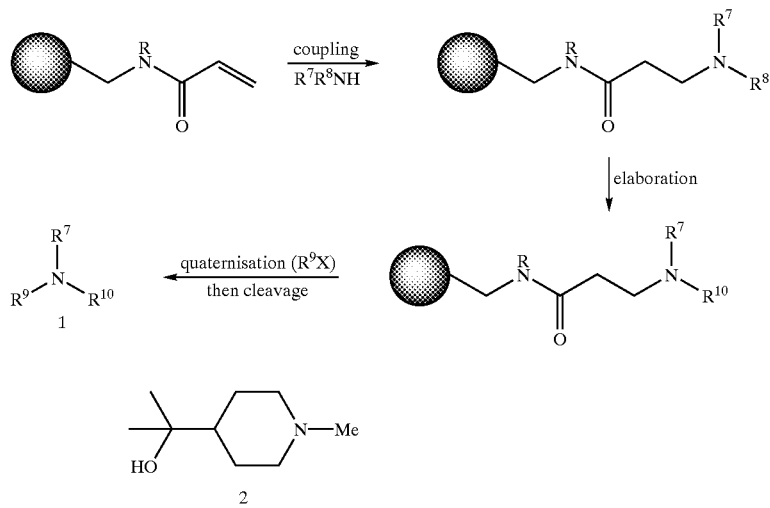

The person skilled in the art will appreciate that if one of the R groups (ie $R^7$, $R^8$ or $R^9$) is removed subsequent to cleavage of the tertiary amine from the resin, a secondary amine will result. An example of a removable group could be p-methoxybenzyl, cleavable under acidic conditions such as TFA. In a variant of the second aspect of the invention a primary amine (instead of a secondary amine) may be used in step (i), giving rise to a secondary amine which may be converted to a tertiary amine by the introduction of a reductive alkylation step under appropriate reaction conditions, prior to the addition of the alkylating agent, such as $R^9X$, of step (ii).

In the case where the amide functionalised support takes the form:

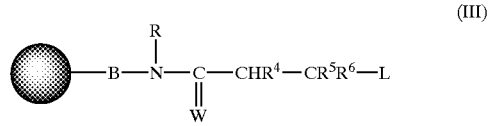

(III)

B, R, W, $R^4$, $R^5$, $R^6$, and L are as defined hereinbefore. Examples of suitable resin derivatives of Formula (III) are as hereinbefore described.

The man skilled in the art will appreciate that the amide functionalised resin of Formula (III) may participate in an alkylation reaction with an appropriate primary or secondary amine to form a compound 3 as per the general description given hereinabove (Route B, Scheme 1).

In a third aspect of the invention there is provided as an intermediate in the obtaining of a tertiary amine a quaternary ammonium compound linked to a support according to the following Formula (IV):

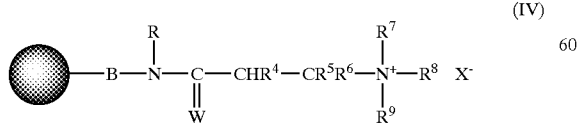

(IV)

wherein B, R, W, $R^4$, $R^5$, $R^6$, $R^7$, $R^8$, and $R^9$ are as defined hereinabove, and $X^-$ is a counteranion, such as $Br^-$, $I^-$, or an acid derived anion.

In a preferred embodiment B is selected from $(CH_2)_n$ and $CH_2(OCH_2CH_2)_n$; n is 0, 1 or 2; R is selected from H, $(C_1-C_4)$ alkyl, and phenyl; W is O; and $R^4$, $R^5$ and $R^6$ are H. In a further preferred embodiment B is $CH_2$; R is selected from H, $CH_3$, $C_2H_5$, $C_3H_7$ (ie straight or branched chain), and phenyl; W is O; and $R^4$, $R^5$ and $R^6$ are H. In a still further preferred embodiment B is $CH_2$; R is H; and $R^4$ $R^5$ and $R^6$ are H.

In a fourth aspect of the invention, there is provided use of an amide functionalised support according to any one of Formulae (I), (III) or (IV) in the synthesis of a tertiary amine, or in the synthesis of N-containing heterocyclic compounds capable of quaternisation.

In a fifth aspect of the invention, there is provided, the use of an amide functionalised support according to any one of Formulae (I), (III), or (IV) in the manufacture of a combinatorial chemistry library or array of compounds.

In a second variant of the invention there is provided a sulphone functionalised solid support of Formula (V).

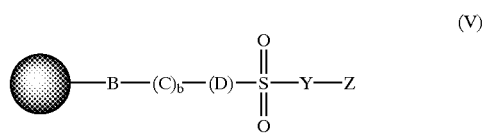

(V)

wherein

represents the solid support;
B is a conventional spacer arm or a bond;
C is O, NR, S, $CH_2$ or $SO_2$;
R is selected from H, $(C_1-C_6)$alkyl, optionally substituted with halogen, aryl$(C_1-C_6)$alkyl and aryl, optionally substituted with $(C_1-C_6)$alkoxy, OH or halogen;
b is an integer selected from 0 and 1;
D is selected from $(C_1-C_6)$alkylene, arylene, optionally substituted with halogen, and arylene$(C_1-C_6)$alkylene: or D is absent;

Y is CHR$^4$ where R$^4$ is selected from H, (C$_1$–C$_4$)alkyl, optionally substituted with halogen, and phenyl, optionally substituted with CF$_3$, (C$_1$–C$_6$)alkoxy;

Z is CR$^5$R$^6$—L where R$^5$ and R$^6$ are independently selected from H, (C$_1$–C$_4$)-alkyl, and phenyl; L is a leaving group; or Y and Z together form CR$^4$=CR$^5$R$^6$ wherein R$^4$ and R$^5$ are as defined above, or wherein R$^4$ and R$^5$ together with the carbon atoms to which they are bonded form a (C$_4$–C$_8$)cycloalkene ring;

with the proviso that when D is absent C is not SO$_2$, S or O, and when D is —CH$_2$—, C is not SO$_2$.

The term (C$_1$–C$_6$)alkylene as used in the definition of formula V means a bivalent radical having 1–6 carbon atoms, such as methylene, ethylene, trimethylene, 1-methylethylene, tetramethylene, pentamethylene, hexamethylene. A preferred (C$_1$–C$_6$)alkylene group is methylene.

The term arylene means a bivalent aromatic radical of an aromatic ring system having from 6–12 carbon atoms, such as for example 1,2-phenylene, 1,3-phenylene, 1,4-phenylene or 1,4-naphthalenediyl; a preferred arylene group is 1,3-phenylene. The remaining terms in the definition of formula V have the meaning as previously given.

Preferred solid supports as used in the sulphone functionalised solid support of Formula (V) include polystyrene based resins. cross-linked to varying degrees with divinylbenzene to give either a microporous or macroporous support, polyethyleneglycol (PEG) or PEG-derivatised polystyrene.

In a preferred embodiment, B is selected from (CH$_2$)$_n$, CH$_2$(OCH$_2$CH$_2$)$_n$, —CH$_2$C(CH$_3$)(PEG)$_2$ and PEG—CH$_2$; n is 1 or 2; C is O or is absent; D is phenylene or is absent; and Y and Z together form CR$^4$=CR$^5$R$^6$ wherein R$^4$, R$^5$ and R$^6$ are independently selected from H, CH$_3$ and phenyl; or Y is CHR$^4$ and Z is CR$^5$R$^6$—L where R$^4$, R$^5$ and R$^6$ are independently selected from H, (C$_1$–C$_4$)alkyl, and phenyl; and L is a leaving group; with the proviso that when D is absent C is not O.

In a further preferred embodiment B is CH$_2$; C is O and D is 1,3-phenylene; or C and D are absent: Y—Z are —CH=CH$_2$; or Y is CH$_2$ and Z is CH$_2$—L where L is a leaving group; and the solid support is the polystyrenedivinylbenzene support of a Merrifield resin.

In a particular preferred embodiment B is CH$_2$; C is O and D is 1,3-phenylene; Y is CH$_2$ and Z is CH$_2$—L where L is Cl; and the solid support is the polystyrenedivinylbenzene support of a Merrifield resin.

Upon attachment of a primary or secondary amine (HNR$^7$R$^8$; derivatives 3 in Scheme 4) to this preferred sulphone functionalised solid support, the derivatised support was found (i) to be stable to alkoxides (e.g. sodium methoxide at room temperature), allowing, for example, transesterification reactions (such as the conversion of ethyl ester into methyl esters), and (ii) to be stable to Grignard reagents (e.g. phenylmagnesium bromide at room temperature), allowing, for example, resin bound esters to be converted to alcohols.

Amine derivatives (derivatives 3 in Scheme 4) prepared from another preferred sulphone functionalised Merrifield derived support according to formula V wherein B is CH$_2$, C and D are absent and X—Y represents CH$_2$—CH$_2$, were found, in addition to being stable to alkoxides and Grignard reagents, to be stable (iii) to strong acids (e.g. 6M HCl in dioxane at reflux) allowing, for example, cyclic ketals to be converted into ketones, to be stable to (iv) nucleophilic hydride reducing agents (e.g. sodium borohydride at room temperature) allowing, for example, imines to be converted to amines, and to be stable (v) to electrophilic hydride reducing agents (e.g. diborane-DMS complex at room temperature) allowing, for example, amides to be converted into amines.

The stability advantages mentioned for the sulphone functionalised supports of the invention in comparison with the prior art REM resins (Morphy et al. supra) allow a much wider range of chemical reactions to be carried out on the supports, and consequently increases the diversity of compound libraries which can be made using the supports of the invention.

Generally, a sulphone-functionalised support of Formula (V) can be prepared from a suitable solid support such as a resin comprising a leaving group, for example a resin of Formula (VI)

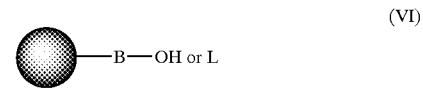

(VI)

where (B) and L are as defined hereinabove. The solid support (VI) may be thiolated with a thiol compound of formula:

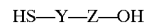

wherein Y and Z are as defined herein. The resulting thioether alcohol may then be oxidised to a sulphone alcohol, followed by substitution of the OH group with an activating group (a leaving group L) such as Br, Cl, tosyloxy, mesyloxy, or trifluoromethanesulphonyloxy. Alternatively, compounds of Formula (V), wherein C is NR and D is absent, can be prepared by acylation of an amine-functionalised solid support with a sulphonyl chloride according to general formula L—Z—Y—SO$_2$—Cl wherein L, Y and Z are as defined herein. Synthesis of a support according to formula V can be illustrated with reference to Scheme 3 where HS—Y—Z—OH is mercaptoethanol, and a representative resin of Formula (VI) is Merrifield resin (a chloromethylated polystyrene resin) available from Novobiochem:

SCHEME 3

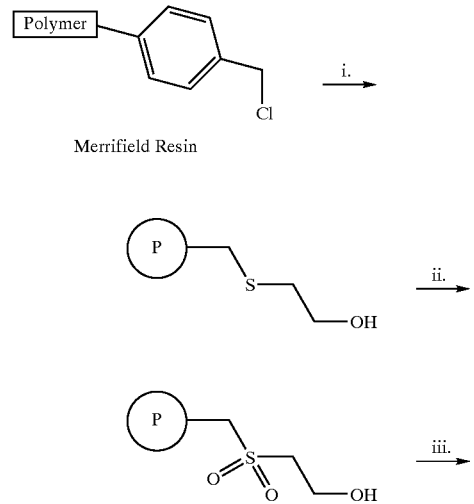

Merrifield Resin

-continued

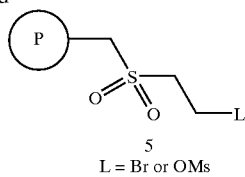

5
L = Br or OMs

[(i) 10 eq. mercaptoethanol/$Cs_2CO_3$, DMF, 20° C., 3 d.;(ii) excess m-CPBA, DCM, 20° C., 12 h (or excess Oxone, aq. DMF, 20° C., 12 h); (iii) $PBr_3$, DCM, 20° C., 16–24 h (or 10 eq. Mesyl Cl. DCM, 20° C., 2 hr.)];

the amide-functionalised synthesis of tertiary amines, it can be seen that compounds 6 can be recycled by re-reacting with more secondary amine (Route A).

Reference is again made to Scheme 4

In an alternative, an amine 8 may then be added to an appropriate resin of choice, such as hydroxymethyl polystyrene 7 to give 3. Alkylation of 3 provides 4 followed by a cleavage reaction giving 6. 6 may then undergo addition of secondary amine giving 3 followed by alkylation and—elimination generating a tertiary amine or N-containing heterocyclic compound with concomitant re-generation of the vinyl sulphone functionalised support.

SCHEME 4

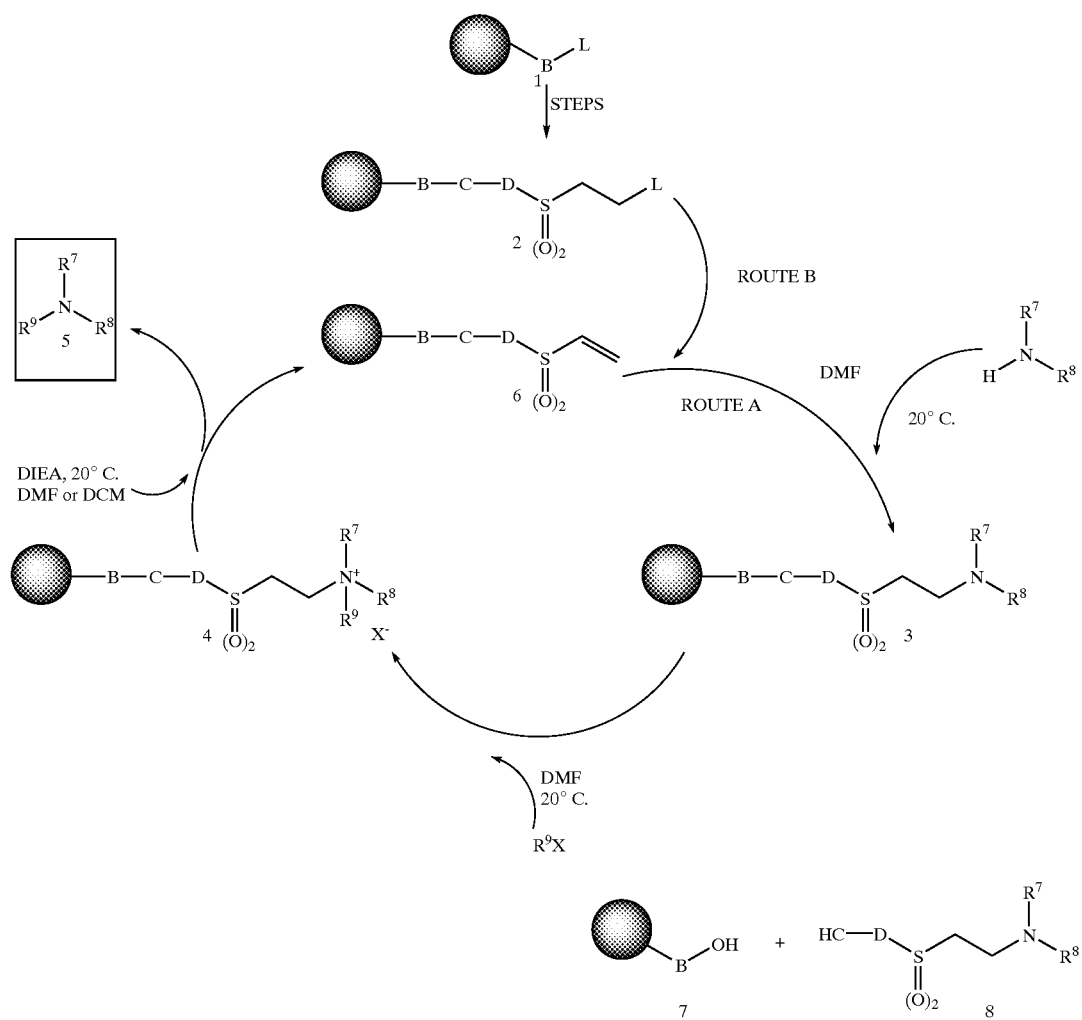

Reference is made to Scheme 4. 2'-Bromoethyl- and 2'-mesyloxyethyl sulfones 2 (L=Br or OMs) can be used as masked forms of a vinyl sulfone 6 in several reactions with secondary amines, such as tetrahydroiso-quinoline (THIQ), piperidines, morpholine, pyrolidine and dioctylamine and the like to give resin-bound tertiary amine products 3 (Route B). After washing, the resin bound tertiary amine products can be treated with an alkylating agent such as allyl bromide, to give quaternised ammonium salts 4, and these may then be treated with DIEA to effect Hofmann elimination and release tertiary amines 5 (as HBr salts) from the resin. As in In a further aspect of the invention there is provided a process for the preparation of a tertiary amine or an N-containing heterocyclic compound which comprises:

(i) adding a primary or secondary amine to a sulphone-functionalised support according to Formula (V) by way of a Michael addition to a vinyl sulphone or by alkylation using an ethyl sulphone having a leaving group in the 3 position forming a tertiary amine;

(ii) adding an alkylating agent forming a quaternary ammonium compound;

(iii) performing a Hofmann elimination on the quaternary ammonium compound generated in step (ii).

In a variant of the above aspect of the invention there is provided a process for the preparation of a tertiary amine which comprises:
(i) adding a primary amine to a sulphone-functionalised support according to Formula (V) by way of a Michael addition to a vinyl sulphone or by alkylation using an ethyl sulphone having a leaving group in the 3 position;
(ii) performing a reduction alkylation on the secondary amine produced in step (i) giving a tertiary amine;
(iii) adding an alkylating agent to the product of step (ii); and
(iv) performing a Hofmann elimination on the quaternary ammonium compound generated in step (iii).

In a third aspect of the invention there is provided as an intermediate in the obtaining of a tertiary amine a quaternary ammonium compound linked to a support according to the Formula (VII):

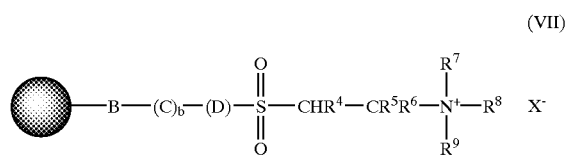

(VII)

wherein B, C, D, $R^4$, $R^5$, $R^6$ $R^7$, $R^8$, $R^9$, and b are as defined hereinabove, and $X^-$ is a counteranion, such as $Br^-$, $I^-$, or an acid derived anion.

B may be any conventional spacer such as $(CH_2)_n$, $CH_2(OCH_2CH_2)_n$, $PEG\text{-}CH_2$, and $-CH_2C(CH_3)(PEG)_2$; and n is 0, 1, 2, 3 or 4.

In a preferred embodiment B is selected from $(CH_2)_n$, $CH_2-(OCH_2CH_2)_n$, $CH_2C(CH_3)(PEG)_2$, and $PEG\text{-}CH_2$; n is 1 or 2; C is O or is absent; D is phenylene or is absent; and $R^4$, $R^5$ and $R^6$ are independently selected from H, $(C_1-C_4)$ alkyl and phenyl: with the proviso that when D is absent C is not O. In a further preferment, B is $CH_2$; C is O and D is phenylene or C and D are absent; and $CHR^4-CR^5R^6$ is $CH_2-CH_2$.

In another aspect of the invention there is provided use of a sulphone-functionalised support according to Formulae (V) or (VII) in the synthesis of a tertiary amine or in the synthesis of an N-containing heterocycle capable of quaternisation.

In a still further aspect of the invention, there is provided use of a sulphone-functionalised support according to Formulae (V) or (VII) in the manufacture of a combinatorial chemistry library or an array of compounds.

It will be appreciated by the skilled adressee that the solid supports which serve as the starting material will be loaded with an amount of linking agent comprising amide or sulphone functionalities which enables chemical synthesis of compounds of interest to proceed. Generally, the amount of linking agent to be loaded onto the resin can be any amount provided that the chemical synthesis of compounds of interest can proceed. Typically, the amount of a linking agent which may be loaded onto the resin can be any amount from 0.05 mmol/gram resin depending on the chemical synthesis contemplated. Generally, the amount of linking agent for loading onto the resin can be between 0.1 and 2.0 mmol/gram resin, more preferably between 0.25 and 1.25 mmol/gram resin and most preferably between 0.4 and 1.0 mmol/gram resin.

There now follow examples which illustrate the invention.

Experimental

Abbreviations: DMSO, dimethylsulfoxide; DMF, dimethylformamide; DCM, dichloromethane; THIQ, tetrahydroisoquinoline; THF, tetrahydrofuran; mCPBA, metachloroperoxybenzoic acid (Aldrich, 85%); DIEA, diisopropylethylamine; DEAD, diethylazodicarboxylate, DIAD, diisopropylazodicarboxylate; PE, petroleum ether (fraction b.p. 40–60° C.); est., estimate; max. est. yield, maximal estimated yield.

NMR spectra are recorded on a Bruker AM-300 (300 MHz; f.t. $^1$H-NMR, andd 74.76 MHZ; $^{13}$C-NMR), Varian gemini 200 (200 MHz; f.t. $^1$H-NMR and 50.31 MHZ; $^{13}$C-NMR). $^1$H-NMR and $^{13}$C-NMR spectra are described in parts per million downfield from TMS and are reported consecutively as position ($\delta_h$ or $\delta_c$), multiplicity (s-singlet, d-doublet, t-triplet, q-quartet, dd-doublet of doublets, ddt doublet of doublets of triplets. m-multiplet and br—broad), relative integral, coupling constant (Hz) and assignment. $^1$H-NMR are referenced internally on $CHCl_3$ (7.25 ppm) or DMSO (2.47 ppm). $^{13}$C-NMR are referenced on $CHCl_3$ (77.0 ppm), or DMSO (39.7 ppm).

IR spectra are recorded on a Perkin-Elmer 1710 f.t. IR spectrometer. The samples were prepared as thin films between sodium chloride discs or KBr disks (2%). The frequencies (v) as absorption maxima are given in wavenumbers ($cm^{-1}$) relative to a polystyrene standard. Intensities are reported as broad—br, strong—st, very strong—vst, medium—m, weak—w. Mass spectra and accurate mass measurements are recorded on VG 70-250 SE Major fragments using the ionisation method indicated are given as percentages of the base peak intensity (100%).

EXAMPLE 1

Amide Resin Synthesis

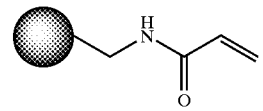

Aminomethyl polystyrene resin (NovaBiochem) (1.0 g, 1.13 mmol) was added to a 15 ml ISOLUTE polypropylene tube. The resin was swollen with a solution of DIEA (1.98 ml, 11.3 mmol) and anhydrous DCM (5 ml) followed by addition of acryloyl chloride (0.92 ml, 11.3 mmol). The vessel was then placed on a Stuart Scientific SB1 tuberotator and agitated for 4 h at room temperature. The amide resin was drained, washed using a VACMASTER station (International Sorbent Technologies) with DCM (3×3 ml), MeOH (3×3 ml) and then dried under vacuum. FT-IR (2% w/w KBr disk): C=0 1675 $cm^{-1}$ (amide).

EXAMPLE 2

Michael Addition

Polymer-bound 4-piperidinecarboxylic Acid, Ethyl Ester

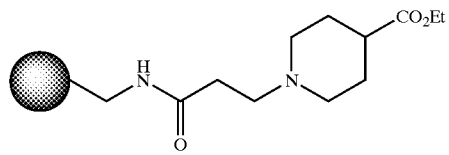

The amide resin (0.5 g, 0.565 mmol) was swollen with a solution of 4-piperidinecarboxylic acid, ethyl ester (Aldrich) (0.87 ml, 5.65 mmol) in DMF (4 ml), in a QUICKFIT test-tube and stirred for 18 h at 50° C. The reaction suspension was cooled to room temperature and the resin was washed using a VACMASTER station with DMF (3×3 ml), DCM (3×3 ml), MeOH (3×3 ml) and then dried under vacuum.

FT-IR (2% w/w KBr disk) C=0 1721 cm$^{-1}$ (ester); 1661cm$^{-1}$ (amide).

EXAMPLE 3

Quaternisation

Polymer-bound 4-piperidinecarboxylic Acid, 1-[(4-nitrophenyl) methyl)] Ethyl Ester

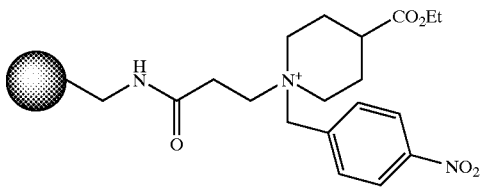

The polymer-bound 4-piperidinecarboxylic acid, ethyl ester resin (0.28 mmol) was swollen with a solution of p-nitrobenzyl bromide (0.61 g, 2.8 mmol) in DMF and was agitated on the tube-rotator for 18 h at room temperature. The resin was drained, washed using a VacMaster station with DMF (3×3 ml), DCM (3×3 ml), MeOH (3×3 ml) and then dried under vacuum. FT-IR (2% w/w KBr disk): C=0 1725 cm$^{-1}$ (ester); 1655 cm$^{-1}$ (amide); 1523 cm$^{-1}$ (NO$_2$).

EXAMPLE 4a

Cleavage from the Amide resin

4-Piperidinecarboxylic acid, 1-[(4-nitrophenyl) methyl] Ethyl Ester

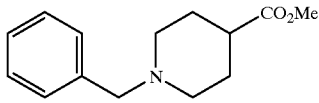

A suspension of the polymer-bound 4-piperidinecarboxylic acid, 1 -[(4-nitrophenyl)methyl]-ethyl resin (0.28 mmol) in THF (4 ml) containing DIEA (98 μl, 2 equiv.) was stirred in a QUICKFIT test-tube overnight, at reflux. The reaction suspension was cooled down to room temperature, drained and the resin washed using a VAC-MASTER station with DCM (2×3 ml). The filtrate was collected and evaporated. The crude material was redissolved in DCM (2 ml) and the resulting solution washed with potassium carbonate (1 ml, 20% aq. sol.), dried over sodium sulphate (0.3 g), filtered and evaporated. The trace amount of plasticizer and DIEA was removed using an ISOLUTE-XL solid phase extraction column, containing 0.5 g of silica. The crude material was loaded in DCM (0.5 ml), eluted with heptane (3 ml, plasticizer elutes) and then ethyl acetate (3 ml. elutes amine). Evaporation of the EtOAc provided the product as a colorless gum.

$^1$H NMR (CDCl$_3$, 400 MHz) 8.17 (d,J=8.7 Hz, 2H), 7.50 (d, J=8.8 hz, 2H), 4.12 (M, 2H), 3.59 (m, 2H), 2.9–1.4 (m, total 9H), 1.23 (t, J=7.1 Hz, 3H).

EXAMPLE 4b 2-(4-nitrobenzyl )-1,2,3,4-tetrahydro-isoguinoline

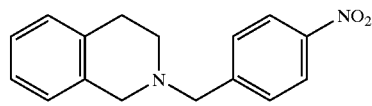

The compound was prepared in a directly analogous fashion to 4a using the procedures and quantities of reagents given in Examples 2, 3 and 4a, but using 1,2,3,4-tetrahydro-isoquinoline (5.65 mmol) instead of 4-piperidinecarboxylic acid ethyl ester in the Michael addition step.

$^1$H NMR (250 MHz) 8.19 (d, J=8.5 Hz, 2H), 7.58 (d. J=8.85 Hz, 2H), 6.95–7.15 (m, 4H), 3.77 (s, 2H), 3.64 (s,2H), 2.92 (t, J=5.8 Hz, 2H), 2.75 (t, J=6.0 Hz, 2H).

EXAMPLE 4c 2-allyl-1,2,3,4-tetrahydro-isoguinoline

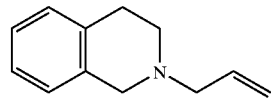

The compound was prepared in a directly analogous fashion to 4a using the procedures given in Examples 2, 3 and 4a, but using 1,2,3,4-tetrahydro-isoquinoline (5.65 mmol) instead of 4-piperidinecarboxylic acid ethyl ester in the Michael addition step and allyl bromide (2.8 mmol) instead of p-nitrobenzyl bromide in the quanternisation step.

$^1$H NMR (250 MHz) 7.01–7.11 (m, 4H), 5.94–5.97 (m, 1H) 5.23 (m, 2H), 3.63 (s, 2H), 3.18 (dt, J=6.41 Hz, 1.23 Hz, 2H), 2.91 (t, J=5.8 Hz, 2H), 2.75 (t, J=6.0 Hz, 2H).

EXAMPLE 4d 1-(4-nitrobenzyl)-4-phenyl-piperazine

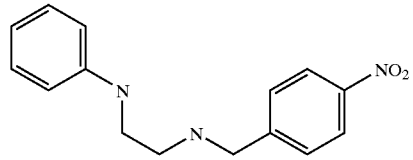

The compound was prepared in a directly analogous fashion to 4a using the procedures given in Example 2, 3 and 4a, but using N-phenyl-piperazine (5.65 mmol) instead of 4-piperidinecarboxylic acid ethyl ester in the Michael addition step.

$^1$H NMR (250 MHz) 8.19 (d, J=8.85 Hz, 2H), 7.54 (d, J=8.85 Hz. 2H), 7.29–7.23 (m, 2H), 6.94–6.83 (m, 3H), 3.65 (s, 2H), 3.20 (t, J=4.9 Hz, 4H 2.62 (t, J=5.05 Hz, 4H).

EXAMPLE 4e

N-(4-nitrobenzyl)-N-methylphenethylamine

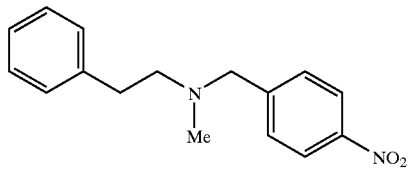

The compound was prepared in a directly analogous fashion to 4a using the procedures given in Examples 2, 3 and 4a, but using N-methylphenethylamine (5.65 mmol) instead of 4-piperidinecarboxylic acid ethyl ester in the Michael addition step. $^1$H NMR (250 MHz) 8.13 (d, J=8.85 Hz, 2H), 7.41 (d, J=8.85 Hz, 2H), 7.32–7.15 (m, 5H), 3.62 (s, 2H), 2.81 (t, J=7.32, 2H), 2.65 (t, J=7.94, 2H), 2.30 (s, 3H).

EXAMPLE 5a

Stability to Aminolysis

Polymer-bound 4-piperidinecarboxylic Acid, Ethyl Ester

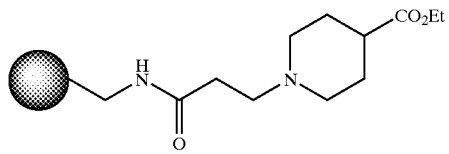

Polymer-bound 4-piperidinecarboxylic acid, ethyl ester resin (example 2) (0.25 g, 0.283 mmol) was swollen with a solution of pyrrolidine (0.19 ml, 2.26 mmol) in DCM (4 ml). Aluminum chloride (75.4 mg, 0.56 mmol) was added as a solid and the resulting suspension was agitated on the tube-rotator for 18 h at room temperature. The resin was drained, washed using the VACMASTER station with DMF (3×3 ml), 20% DIEA/DCM (3×3 ml), DCM (3×3 ml), MeOH (3×3 ml) and then dried under vacuum.

FT-IR (2% w/w KBr disk): C=0 1729 cm$^{-1}$ (ester); 1639 cm$^{-1}$ (br) (amide).

EXAMPLE 5b

4-Piperidinecarboxylic Acid, 1-[(4-nitrophenyl)methyl]-ethyl Ester

The product of example 5(a) was alkylated and cleaved according to the procedure of examples 3 and 4 to give 5b.

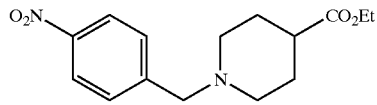

EXAMPLE 6a

Stability to TFA

Polymer-bound 4-piperidinecarboxylic Acid, Ethyl Ester

A suspension of the polymer-bound 4-piperidinecarboxylic acid, ethyl ester resin (example 2) (0.25 g, 0.283 mmol) in 95% TFA—5% H$_2$O solution (4 ml) was heated at reflux in a QUICKFIT test-tube, for 18 h. The reaction suspension was cooled to room temperature, drained, washed using a VACMASTER with DCM (3×3 ml), 20% DIEA/DCM (3×3 ml), DCM (3×3 ml), MeOH (3×3 ml) and then dried under vacuum.

FT-IR (2% w/w KBr disk): C=O 1723 cm$^{-1}$ (ester), 1662 cm$^{-1}$ (amide).

EXAMPLE 6b

4-Piperidinecarboxylic Acid, 1-[(4-nitrophenyl)methyl]-ethyl Ester

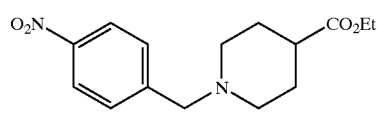

The product of example 6a was alkylated and cleaved according to the procedure of examples 3 and 4 to given 6b.

EXAMPLE 7a

Lithium Borohydride Reduction

Polymer-bound 4-piperidinemethanol

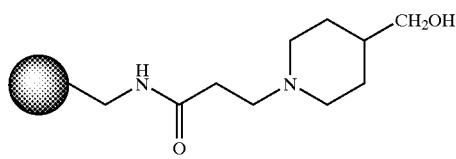

Polymer-bound 4-piperidinecarboxylic acid, ethyl ester (0.25 g, 0.283 mmol) was swollen with a solution of MeOH (0.11 ml, 2.83 mmol) in THF (4 ml) in a QUICKFIT test-tube. Lithium borohydride (1.4 ml, 2.83 mmol) was added under nitrogen atmosphere and the resulting suspension was then stirred overnight at reflux. The resin was drained, washed using VACMASTER with DMF (3×3 ml), DCM (3×3 ml), MeOH (3×3 ml) and then dried under vacuum. FT-IR (2% w/w KBr disk: C=0 1654 cm$^{-1}$ (amide).

EXAMPLE 7b

1-[(4-Nitrophenyl)methyl], 4-piperidinemethanol

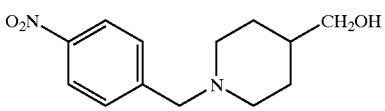

The product of example 7a was alkylated and cleaved according to the procedure of examples 3 and 4. $^1$H NMR (CDCl$_3$, 400 MHz) 8.17 (d, J=8.7 Hz, 2H), 7.50 (d, J=8.6 Hz. 2H), 3.58 (s, 2H), 3.51 (d, J=6.4 Hz, 2H), 2.86 (d, J=11.4 Hz, 2H). 2.02 (dt, J=2.4 and 11.6 Hz, 2H), 1.73 (d, J=13.2, 2H), 1.41–1.17 (m, 3H).

EXAMPLE 8a

Transesterification

Polymer-bound piperidinecarboxylic Acid, Methyl Ester

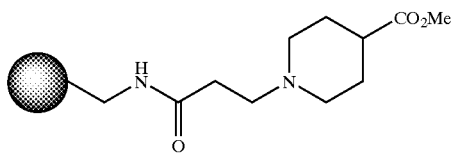

Polymer-bound piperidinecarboxylic acid, ethyl ester resin (0.25 g, 0.283 mmol) was swollen with a solution of MeOH (1 ml) in THF (4 ml) in a QUICKFIT test-tube. After addition of sodium methoxide (0.28 ml, 0.028 mmol, 1M solution in MeOH) the resulting suspension was stirred overnight at reflux. The reaction suspension was cooled down to room temperature and the resin was washed using VACMASTER station with DCM (4×3 ml), MeOH (2×3 ml) and then dried under vacuum. FT-IR (2% w/w KBr disk): C=O 1736 $cm^{-1}$ (ester); 163 $cm^{-1}$ (amide).

EXAMPLE 8b

Piperidinecarboxylic Acid, 1-benzyl Methyl Ester

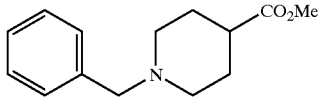

The example of 8a was alkylated with benzyl bromide and cleaved according to the procedure of examples 3 and 4 to give product compound 8b.

EXAMPLE 9a

Grignard Reaction

Polymer-bound 4-piperidinemethanol, Alpha, Alpha-dimethyl

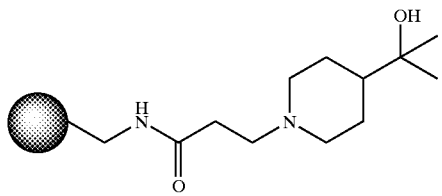

Polymer-bound piperidinecarboxylic acid, ethyl ester (0.25 g, 0.283 mmol) was swollen with THF (4 ml). Methylmagnesium bromide (0.47 ml, 1.4 mmol, 3M solution in ether) was added dropwise under a nitrogen atmosphere, at 0° C. (ice-bath). The suspension was allowed to reach room temperature and then stirred overnight. The reaction was quenched with ammonium chloride (0.5 ml, saturated aq. sol.) and the resin was then drained, washed using VACMASTER station with DMF (3×3 ml), DCM (3×3 ml), MeOH (3×3 ml) and then dried under vacuum. FT-IR (2% w/w KBr disk): C=O 1654 $cm^{-1}$ (amide).

EXAMPLE 9b

1-Methyl 4-piperidinemethanol, Alpha, Alpha-dimethyl

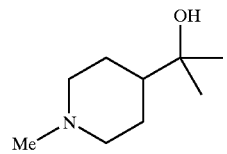

The example of 9a was alkylated with methyl iodide and cleaved according to the procedure of examples 3 and 4 to give product compound 9b.

EXAMPLE 9c

Grignard Reaction

Polymer-bound 4-piperidinemethanol, Alpha, Alpha-diphenyl

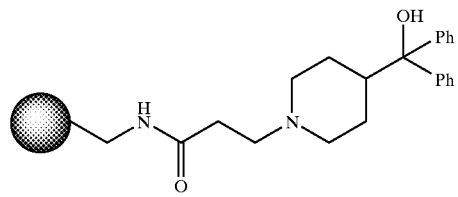

Polymer-bound piperidinecarboxylic acid, ethyl ester (0.25 g, 0.283 mmol) was swollen with THF (4 ml). Phenylmagnesium bromide (1.37 ml, 1.4 mmol, 1M solution in THF) was added dropwise under nitrogen atmosphere, at 0° C. (ice-bath). The suspension was allowed to reach room temperature and then stirred overnight. The reaction was quenched with ammonium chloride (0.5 ml, saturated aq. sol.) and the resin was then drained, washed using VACMASTER station with DMF (3×3 ml), DCM (3×3 ml), MeOH (3×3 ml) and then dried under vacuum.

FT-IR (2% w/w KBr disk): C=O 1630 $cm^{-1}$ (amide).

EXAMPLE 9d 1-methyl4-piperidinemethanol, Alpha, Alpha-diphenyl

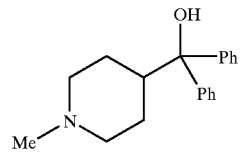

The example of 9c was alkylated with methyl iodide and cleaved according to the procedure of examples 3 and 4 to give product compound 9d.

The above examples 5(a), 5(b), 6(a), 6(b), 7(a), 7(b) and 9(a)–9(b) show that the amide functionalised resin is stable under rigorous reaction conditions, for example TFA, aminolysis, lithium borohydride reduction and, when R=H, also with respect to Grignard reagents.

EXAMPLE 10

2-Hydroxyethyl-thiomethyl-polystyrene (1)

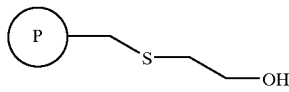

Method A: Merrifield resin.(Novabiochem, 0.76 mmol g$^{-1}$, 5 g, 3.8 mmol) was suspended in dry DMF (40 cm$^3$) and a solution of sodium 2-hydroxyethanethiolate, freshly prepared from NaH (12.5 mmol, 500 mg, 60% in mineral oil) and 2-hydroxyethanethiol (12.8 mmol, 0.9 cm$^3$) in DMF (25 cm$^3$), was added. The suspension was stirred at 60° C. for 4 h then at 90° C. for 1 h and then overnight at 20° C. The resin was removed by filtration, washed successively with DMF, DCM, H$_2$O, DCM, MeOH/H$_2$O, DCM/DMF and with MeOH (50 cm$^3$, each of them). The resin was dried under high vacuum with warming to 50° C.

IR ($_{max}$/cm$^{-1}$, 2% in KBr): 3500 (st), 3462 (br, OH), 1601, 1493, 1452 (st, polystyrene), 1059 (m), 1025 (m).

Method B: Merrifield resin (Novabiochem, 0.76 mmol g$^{-1}$, 3.8 g, 2.9 mmol) in dry DMF (20 cm$^3$) was treated with 2-hydroxyethanethiol (15.25 mmol, 1 cm$^3$). The suspension was stirred for 4 h at 95° C. It was left over night at 20° C. The resin was filtered off and washed extensively with DMF, DCM, H$_2$O, H$_2$O/MeOH (1:1) and then pure MeOH and finally dried under high vacuum at 50° C.

Method C: Merrifield resin (Novabiochem, 0.76 mmol g$^{-1}$, 1.96 g, 1.45 mmol) in dry DMF (50 cm$^3$) was treated with Cs$_2$CO$_3$ (2.98 mmol, 0.971 g) and 2-hydroxyethanethiol (14.96 mmol, 1.045 cm$^3$). After stirring for 2 d at 20° C. the resin was drained and washed like in the cases A and B and dried at 45° C. under high vacuum.

IR ($_{max}$/cm$^{-1}$, 2% in KBr): 3425 (br, OH), 1601, 1493, 1453 (st, polystyrene), 1061 (m), 1029 (m).

EXAMPLE 11

2-Hydroxyethyl-sulfomethyl-polystyrene (2)

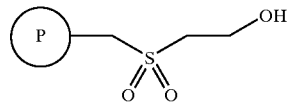

Resin 1 (0.7 mmol g$^{-1}$ (est.), 1.5 g) was treated with mCPBA (5.2 mmol, 1.05 g). The suspension warmed up to 35° C. for a short time and was stirred at 20° C. for 2 d.

After filtration the resin was washed with large quantities of MeOH, DCM, H$_2$O and MeOH, and dried at 50° C. under high vacuum.

IR ($_{max}$/cm$^{-1}$, 2% in KBr): 3511 (br, OH), 1601, 1493, 1453 (st, polystyrene), 1317, 1119 (St, SO$_2$), 1061 (m), 1029 (m).

EXAMPLE 12

Vinylsulfomethylpolystyrene (3) and N-allyl Tetrahydroisoquinoline HBr (4)

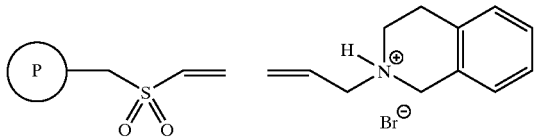

Method A: resin 2 (0.65 mmol g$^{-1}$ (est.), 1.49 g) in dry DCM (25 cm$^3$) was treated with PBr$_3$ (2.28 mmol, 216 mm$^3$) at 20° C. for 12 h. The resin was filtered off, washed with DCM (200 cm$^3$), dried in air and transferred to a flask with DMF (20 cm$^3$) and THIQ (5.7 mmol, 725 mm$^3$) was added. The resin was stirred at r.t. for 24 h. washed with DMF, MeOH, DCM, and MeOH. It was dried under high vacuum. 1.45 g (0.5 mmol g$^{-1}$ (est.)) of it was resuspended in DMF (10 cm$^3$) and allyl bromide (150 mm$^3$, 1.7 mmol) was added. After 5 d at 20° C. the solid was filtered off, washed with DMF (100 cm$^3$) and DCM (100 cm$^3$). The resin was then treated with DIEA (1.00 mmol, 175 mm$^3$) in DCM (25 cm$^3$). After 2 days the solid material resin was filtered off and washed with DCM and MeOH. The solvent was removed from the filtrate and gave analytically pure 4 as a white solid.

3: IR ($_{max}$/cm$^{-1}$, 2% in KBr): 1727 (m), 1600, 1491, 1450 (st, polystyrene), 1320, 1119 (st, SO$_2$).

4: $^1$H-NMR ( /ppm, 300 MHz, CDCl$_3$): 12 (s, br, 1H, HBr), 7.30–7.08 (m, 4H, aromatics), 6.33 (ddt, 1H, J$^{cis}$=10.0 Hz, J$^{trans}$=17.15 Hz, $^3$J=7.14 Hz, CH$_2$—CH=CH$_2$), 5.61–5.5 (m, 2H, CH$_2$—CH=CH$_2$), 4.35 (br m, 2H, N—CH$_2$—Ph), 3.76 (d, 2H, $^3$J=7.14 Hz, CH$_2$—CH=CH$_2$), 3.42 (br m, 4H, N—CH$_2$—CH$_2$—Ph).

Method B: 2 (0.6 mmol g$^{-1}$ (est.), 0.57 g) in dry DCM (30 cm$^3$) was treated with triethylamine (3.4 mmol, 4.78 mm$^3$) followed by mesyl chloride (1.72 mmol, 133 mm$^3$) at 20° C. With addition the suspension became yellow and warms up slightly. It was stirred at ambient temperature for 12 h and the resin was filtered off, washed with DCM (200 cm$^3$) and transferred into a sintered plastic tube with DMF (7 cm$^3$). In the presence of THIQ (1.7 mmol, 216 mm$^3$) the resin was agitated for 8 h, washed again with DMF and treated with allyl bromide (3.4 mmol, 300 mm$^3$) in DMF (3.4 mmol, 600 mm$^3$) and DCM (7 cm$^3$) was added to the resin. After 12 h agitation the resin was washed with DCM and MeOH as in method A and the solvent removed from the combined filtrates. The resin was dried at 50° C. in an oven under vacuum.

The amine 4 was liberated from its HBr salt with K$_2$CO$_3$ solution (2M, 10 cm$^3$) extracted into EtOAc. The organic layer was dried over K$_2$CO$_3$, filtered and the solvent removed, yielding 4.

3: IR ($_{max}$/cm$^{-1}$, 2% in KBr): 1727 (m), 1600, 1491, 1449 (st, polystyrene), 1313, 1117 (st, SO$_2$), 1026 (m).

4 (parent amine): $^1$H-NMR ( /ppm, 300 MHz, CDCl$_3$): 7.14–7.01 (m, 4H, aromatics), 5.96 (ddt, 1H, J$_{cis}$=9.9 Hz, J$_{trans}$=17.15 Hz, $^3$J=6.6 Hz, CH$_2$—CH=CH$_2$), 5.3–5.18 (m, 2H, CH$_2$—CH=CH$_2$), 3.63 (s, 2H, N—CH$_2$—Ph), 3.18 (dt, 2H, $^3$J=6.5 Hz, $^4$J=1.37 Hz, CH$_2$—CH=CH$_2$), 2.92 (t, 2H, $^3$J=5.8 Hz, N—CH$_2$—CH$_2$—Ph), 2.75 (t, 2H, $^3$J=5.8 Hz, N—CH$_2$CH$_2$—Ph).

EXAMPLE 13

3-Methoxy-1-(2'chloroethyl)thiophenol (5)

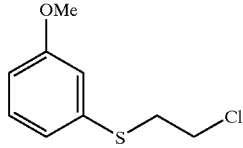

N-Chlorosuccinimide (25.9 mmol, 2.86 g) was suspended in dry DCM (50 cm$^3$). Slowly, 3-methoxythiophenol (25 mmol, 3.1 cm$^3$) was added. After addition of 1 cm$^3$ the suspension turned orange and warmed up. It was cooled for one minute with water and the remaining thiol was added in one go. The orange solution became clear and after 15 minutes a precipitate of succinimide forms from the solution. After an additional 15 minutes of stirring at 20° C. the flask was filled with ethene. The suspension turned almost colorless, the solvent was removed and the residue stirred in carbon tetrachloride (50 cm$^3$). Filtration and removal of the solvent gave crude 5 which was used in the following reaction.

5: $^1$H-NMR ( /ppm, 200 MHz, CDCl$_3$): 7.29–7.21 (m, IH, aromatic), 7.12–6.94 (m, 2H, aromatics), 6.93–6.75 (m, IH, aromatics), 3.83 (s, 3H, OMe), 3.77–3.59 (m, 2H, —S—CH$_2$), 3.28–3.19 (m, 2H, Cl—CH$_2$).

EXAMPLE 14

3-Methoxyl-1-(2'-chloroethyl)phenylsulfone (6)

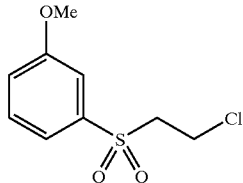

Crude 5 (24.2 mmol, 4.90 g) was dissolved in DCM (80 cm$^3$) cooled to 0° C. and mCPBA (48 mmol, 9.7 g) was added in portions. The reaction was stirred overnight and again treated with mCPBA (24.6 mmol, 5 g) in additional DCM (100 cm$^3$). Ether (100 cm$^3$) was used to dilute the suspension after 24 h and the organic layer was washed thoroughly with Na$_2$CO$_3$ solution (5%, 100 cm$^3$). Three washings with Na$_2$CO$_3$ (5%), brine and drying over MgSO$_4$ followed. M.P. 50.3° C.

6: $^1$H-NMR ( /ppm, 200 MHz, CDCl$_3$): 7.52–7.35 (m, 3H, aromatics), 7.26–7.22 (m, 1H, aromatic), 3.89 (s, 3H OMe), 3.80–3.72 (m, 2H, —SO$_2$—CH$_2$), 3.57–3.49 (m, 2H, Cl—CH$_2$).

IR ($_{max}$/cm$^{-1}$, film): 1310, 1146 (st, SO$_2$), 1251, 1034 (Ph—O—Me).

EXAMPLE 15

3-Hydroxyl-1-(2'-chloroethyl)phenylsulfone (7)

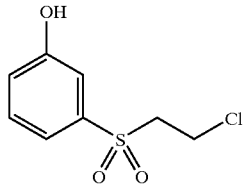

To 6 (8.95 mmol, 2.1 g) in dry DCM (50 cm$^3$) was added IM BBr$_3$ (27 mmol, 27 cm$^3$) in DCM at 0° C. The solution was allowed to reach 20° C. over night, poured into ice water (100 cm$^3$) and stirred for 1.5 h. The aqueous layer was saturated with NaCl and extracted with DCM. The combined organic layers were dried over MgSO$_4$. Filtration and removal of the solvent gave 7 as a white solid An analytical sample was obtained by recrystallisation from DCM (mp: 107.6° C.).

7: $^1$H-NMR ( /ppm, 300 MHz, CDCl$_3$: 7.51–7.41 (m, 3H, aromatics), 7.26–7.15 (m, 1H, aromatic), 6.10 (br s, 1H, OH), 3.77–3.72 (m, 2H, —SO$_2$—CH$_2$), 3.57–3.51 (m, 2H, Cl—CH$_2$).

IR ($_{max}$/cm$^{-1}$, film): 3390 (s,OH), 1304, 1148 (st, SO$_2$).

EXAMPLE 16

3-Hydroxy-1-phenylvinylsulfone (8)

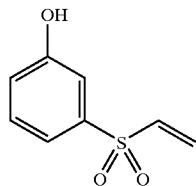

7 (7.3 mmol, 1.6 g) suspended in DCM (50 cm$^3$) was slowly treated with DBU (10.9 mmol, 163 cm$^3$) at 0° C. After 10 minutes a second portion of DBU (3.3 mmol, 50 cm$^3$) was added and the solution allowed to stir at 20° C. for 1.5 h. It was then poured into 2% HCl (18 cm$^3$) and Et$_2$O (150 cm$^3$) was added. The organic layer was washed with IM HCl (2×10 cm$^3$) and brine, and dried over MgSO$_4$. After filtration and removal of the solvent the product was taken up in DCM and two spoonsful of charcoal was added to the yellow solution. It was filtered through plug of silica, prewashed with PE/EtOAc (1:1). The filtrate was evaporated and gave under high vacuum a colorless solid.

8: $^1$H-NMR ( /ppm, 300 MHz, CDCl$_3$): 7.46–7.39 (m, 3H, aromatics), 7.16–7.11 (m, 1H, aromatic), 6.67 (dd, 1H, $^{trans}$J=16.5 Hz, $^{cis}$J=9.89 Hz, H$^{gem}$). 6.64 (d, 1H, $^{trans}$J=16.5 Hz, H$^{cis}$), 6.55 (s, 1H, OH), 6.07 (d, 1H, $^{cis}$J=9.89 Hz, H$^{trans}$).

IR ($_{max}$/cm$^{-1}$, film): 3391 (st, OH), 1301, 1138 (st, SO$_2$).

EXAMPLE 17

3-Hydroxy-1-(2'-[N-tetrahydroisoquinoline]ethyl)phenyl-sulfone (9)

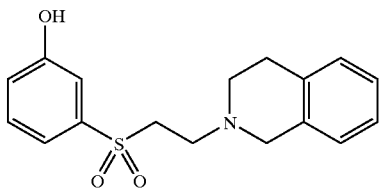

8 (5.43 mmol, 1 g) in DCM (25 cm$^3$) was treated dropwise with THIQ (6.25 mmol, 797 mm$^3$) at room temperature. After 12 h precipitated 9 was filtered off as a white solid, washed with PE, and dried under high vacuum. mp: 177.0° C.

9: $^1$H-NMR (ppm, 300 MHz, (D$_6$)DMSO): 10.17 (s, 1H, OH), 7.43–7.25 (m, 3H, aromatics), 7.08–6.93 (m, 5H, aromatics), 3.55 (t (br), 2H, $^3$J=7.14 Hz, —SO$_2$—CH$_2$), 3.48 (s, 2H, N—CH$_2$—Ph), 2.73 (t (br), 2H, $^3$J=7.40 Hz, —SO$_2$—CH$_2$—CH$_2$—N), 2.66–2.55 (m (br), 4H, N—CH$_2$—CH$_2$—Ph).

IR ($_{max}$/cm$^{-1}$, film): 3441 (st, OH), 1304, 1140 (st, SO$_2$).

EXAMPLE 18

Methylene-3-oxy-1-(2'-chloroethyl)phenylsulfone polystyrene

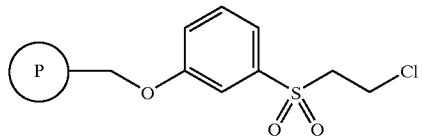

To dry hydroxymethyl polystyrene resin (1.16 mmol g$^{-1}$, 431 mg) suspended in DCM/THF (1:1; 33 cm$^3$), DEAD (2 mmol, 315 mm$^3$) and 7 (4 mmol, 880 mg) were added. Triphenylphosphine (2 mmol, 524 mg) was added slowly, and the cleared suspension was stirred at 20° C. After 3 h the resin was filtered off and washings with DCM/THF (1:1; 3×30 cm$^3$), DCM (3×3 cm$^3$), iPrOH (3×30 cm$^3$) and MeOH followed. The resin was dried at 45° C. under vacuum.

10: IR ($_{max}$/cm$^{-1}$, 2% in KBr): 1600, 1493, 1453 (st. polystyrene), 1319, 1147 (st, SO$_2$), 1226 (st, —O—Ph).

EXAMPLE 19

Methylene-3-oxy-1-phenylsulfone(2'-(N-tetrahydroiso-quinoline)ethyl) polystyrene (11)

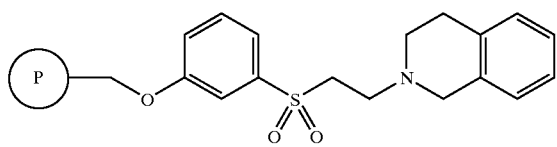

To dry hydroxymethyl polystyrene resin (1.16 mmol g$^{-1}$, 431 mg) suspended in DCM/THF (1:1) (33 cm$^3$), DIAD (2.5 mmol, 483 mm$^3$), 9 (2.5 mmol. 790 mg) and triphenylphosphine (2.5 mmol, 655 mg) were added slowly. With the addition of triphenylphosphine the sulfone dissolved and the suspension, decolorized. After 18 h the resin was filtered and washed with DCM/THF (1:1; 3×40 cm$^3$), THF (50 cm$^3$), MeOH, iPrOH, THF, DCM, iPrOH, and MeOH, and then again with DMSO, DMF, DCM and MeOH (all 50 cm$^3$). The resin was dried at 50° C. under vacuum.

11: IR ($_{max}$/cm$^{-1}$, 2% in KBr): 1600, 1493, 1453 (st, polystyrene), 1312, 1140 (st, SO$_2$), 1247 (st, —O—Ph).

EXAMPLE 19A

Stability of Methylene-3-oxy-1-phenylsulfone(2'-(N-tetrahydroisoquinoline)ethyl) polystyrene (11)

Methylene-3-oxy-1-phenylsulfone(2'-(N-tetrahydroisoquinoline)ethyl) polystyrene (11) was completely stable to 12.5 equivalents of 1.5% trifluoroacetic acid in dichloromethane for 24 hours at 20° C. The acid-treated support alkylated with allylbromide and processed as described in Example 20 to give the expected N-allyl tetrahydroisoquinoline (4) in 81% yield.

The derivatised resin 11 remained completely intact following treatment with 20 equivalents of sodium methoxide in tetrahydrofuran for 3 hours at 21° C., demonstrating the stability of the resin to basic nucleophiles.

EXAMPLE 20

Methylene-3-oxy-1-phenylvinylsulfone polystyrene (12) and N-allyl tetrahydroisoquinoline (4)

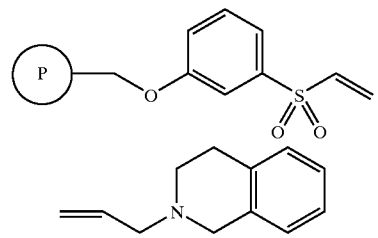

11 (0.97 mmol g$^{-1}$ (est.), 450 mg) in DMF (7 cm$^3$) was treated with allyl bromide (8.75 mmol, 760 mm$^3$) and agitated on a tube rotator for 15 h. The polymer was washed with several small portions of DMF, resuspended in DMF (7 cm$^3$) and treated with methyl iodide (8.75 mmol, 545 mm$^3$) and rotated under light protection for 6 h. The resin was washed with DCM, MeOH and DCM, then was resuspended in DCM (7 cm$^3$) and DIEA (2.93 mmol, 510 mm$^3$) was added. The base decolorized the material immediately. After 18 h shaking, the resin was drained and washed with DCM and MeOH and dried under high vacuum in an oven at 50° C.

The filtrate was evaporated and gave 167 mg of white solid. It was treated with 2M K$_2$CO$_3$ (10 cm$^3$) and extracted five times into DCM. The combined organic phases were washed with brine and dried over K$_2$CO$_3$. Filtration and removal of the solvent gave colorless 4 (parent amine) as an oil.

12: IR ($_{max}$/cm$^{-1}$, 2% in KBr): 1598, 1493, 1452 (st. polystyrene), 1312, 1141 (st, SO$_2$), 1222 (st, —O—Ph).

4: $^1$H-HMR is identical with an authenticated sample.

EXAMPLE 21

2-Bromoethyl-sulfomethyl polystyrene (13)

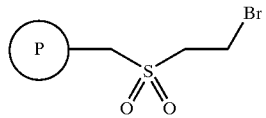

Resin 2 (0.6 mmol g$^{-1}$ (est.), 1.6g; see Example 11) in dry DCM (25 cm$^3$) was treated with PBr$_3$ (10.5 mmol, 1 cm$^3$) and stirred slowly at r.t. for 24 h. The resin was filtered off, washed with DCM (100 cm$^3$) and MeOH (100 cm$^3$).

13: IR ($_{max}$/cm$^{-1}$, 2% in KBr): 1601, 1493, 1453 (st, polystyrene), 1326, 1123 (st, SO$_2$), 1074, 1029 (st).

EXAMPLE 22

N-Allyl-N,N-di-n-octylamine (14)

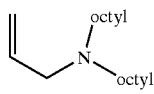

Vinylsulfomethylpolystyrene resin 3 (0.42 mmol g$^{-1}$ (est), 160 mg) in DMF (2 cm$^3$) was treated with dioctylamine (1.7 mmol, 515 mm$^3$) at 20° C. for 24 h. The resin was washed with DMF (10×5 cm$^3$) and DCM (10 cm$^3$), resuspended in DMF (2 cm$^3$) and treated with allyl bromide (4.25 mmol, 365 mm$^3$) at 20° C. for 24 h. The solvent and the reagent was then removed by filtration and the resin washed with DCM (2×20 cm$^3$). The elimination was performed in DCM (4 cm$^3$) with DIEA (1.72 mmol, 300 mm$^3$) overnight. The filtrate of this last reaction step was combined with the DCM and MeOH, washed (25 cm$^3$) from the resin and evaporated. It gave 14 contaminated with DIEA in 38 mg yield. The amine was transferred in a little DCM (<5 cm$^3$) to a K$_2$CO$_3$ covered dry silica column (5 g). Impurities were washed away with hexane and the amine eluted with ethyl acetate. After the removal of the solvent 14 was obtained as a colorless oil.

IR of resin: identical to f.t. IR of resin 3.

14: $^1$H-NMR ( /ppm, 300 MHz, CDCl$_3$) 5.86 (ddt, 1H, $^3$J=6.6 Hz, J$^{cis}$=10.15 Hz, J$^{trans}$=16.65 Hz, CH$_2$—CH=CH$_2$), 5.19–5.08 (m, 2H, CH$_2$—CH=CH$_2$), 3.08 (t br, 2H, $^3$J=6.5 Hz. CH$_2$—CH=CH$_2$), 2.42–2.38 (m, 4H, 2×N—CH$_2$—CH$_2$—), 1.47–1.26 (m, 24H, 2×N—CH$_2$—(CH$_2$)$_6$—CH$_3$), 0.87 (t br, 6H, $^3$J=6.73 Hz, N—CH$_2$(CH$_2$)$_6$—CH$_3$).

EXAMPLE 23:

Methylene-3-oxy-1-[N-(2'-(ethyl isonipecotate) ethyl)]phenyl-sulfone Polystyrene (15)

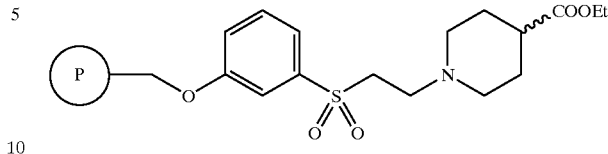

Methylene-3-oxy-1-phenylvinylsulfone polystyrene (12, 0.7 mmol g$^{-1}$ (est.), 300 mg) was treated with ethyl isonipecotate (ethyl 4-piperidinecarboxylate; 3 mmol, 462 mg) at 20° C. overnight. The resin was then washed with DCM and MeOH and dried under vacuum at 50° C.

15: IR ( $_{max}$/cm$^{-1}$, 2% in KBr): 1736 (st, C=O), 1599, 1491, 1438 (st, polystyrene), 1315, 1145 (st, SO$_2$), 1249 (st, —O—Ph).

EXAMPLE 23a

Methylene-3-oxy-1-[N-(2'-(ethylisonipecotate)ethyl)]phenylsulfone polystyrene (15) was treated with 6 equivalents of phenylmagnesium-bromide in tetrahydrofuran. Following alkylation with methylbromide and subsequent treatment with diisopropylethylamine, the expected diphenyl, N-methylpiperidin4-yl carbinol was obtained in 90% recovery.

We claim:

1. A solid support comprising a functionalised sulphone of Formula V:

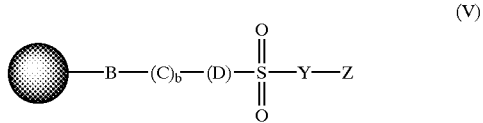

(V)

wherein

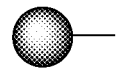

represents the solid support and is the polystyrenedivinylbenzene support of a Merrifield resin;

B is CH$_2$;

C is O;

b is an integer selected from 0 to 1;

D is 1, 3-phenylene;

Y is CH$_2$;

Z is CH$_2$—L wherein L is Cl or Br.

* * * * *